United States Patent
Oishi et al.

(10) Patent No.: US 8,334,132 B2
(45) Date of Patent: Dec. 18, 2012

(54) PROCESS FOR PRODUCTION OF A BETAINE SUCH AS CARNITINE

(75) Inventors: Kosuke Oishi, Yokohama (JP); Eiji Sato, Yokohama (JP); Hiroyuki Mori, Yokohama (JP); Akira Yoshioka, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 662 days.

(21) Appl. No.: 12/514,000

(22) PCT Filed: Nov. 9, 2007

(86) PCT No.: PCT/JP2007/072237
§ 371 (c)(1),
(2), (4) Date: Jul. 7, 2009

(87) PCT Pub. No.: WO2008/056827
PCT Pub. Date: May 15, 2008

(65) Prior Publication Data
US 2009/0325246 A1    Dec. 31, 2009

(30) Foreign Application Priority Data
Nov. 9, 2006 (JP) .................................. 2006-303972

(51) Int. Cl.
*C12P 41/00*    (2006.01)
(52) U.S. Cl. ....................................................... 435/280
(58) Field of Classification Search ........................ None
See application file for complete search history.

(56) References Cited

U.S. PATENT DOCUMENTS

| 4,255,449 A | 3/1981 | Cavazza et al. |
| 4,413,142 A | 11/1983 | Fiorini et al. |
| 4,415,589 A | 11/1983 | Cavazza et al. |
| 4,865,771 A | 9/1989 | Francalanci et al. |
| 5,166,061 A * | 11/1992 | Nakamura et al. ............ 435/128 |

FOREIGN PATENT DOCUMENTS

| DE | 1543847 A1 | 7/1970 |
| GB | 1075562 A | 7/1967 |
| GB | 1367 435 | 11/1973 |
| GB | 2 008 578 A | 11/1978 |
| JP | 49-11828 A | 2/1974 |
| JP | 53-13611 A | 5/1978 |
| JP | 54-76830 A | 6/1979 |
| JP | 54-113409 A | 9/1979 |
| JP | 57-165352 A | 10/1982 |
| JP | 60-258487 A | 12/1985 |
| JP | 62-272983 A | 11/1987 |
| JP | 1-287065 | 11/1989 |
| JP | 02-027995 A | 1/1990 |
| JP | 02-142758 A | 5/1990 |
| JP | 4-278089 A | 10/1992 |
| JP | 4-365491 A | 12/1992 |
| JP | 58-88312 A | 5/1993 |
| JP | 2002-241357 A | 8/2002 |
| JP | 2002-529528 A | 9/2002 |
| JP | 2002-544252 A | 12/2002 |
| JP | 2004-182607 A | 7/2004 |
| WO | WO-00/29370 A1 | 5/2000 |
| WO | WO-00/69808 A1 | 11/2000 |

OTHER PUBLICATIONS

English abstract from CA, AN 118:146302 for JP 04-365491, Dec. 1992.*
Nakamura et al., "A new enzymic synthesis of (R)-gamma-chloro-beta-hydroxybutyronitrile", Tetrahedron 50 (41) : 11821-26 (1994).*
Lorenz, I., "IR-spektroskopische Untersuchungen uber beta-Homobetainamid, gamma-Butyrobetainamid und die Konglomeratbildung beim kirstallinen razemischen Carnitinamid/ The. Infrared Spectra of Some Low-molecular Aliphatic Amides with Quaternary Nitrogen Intrared Spectroscopical Investigations of beta-Homobetaine Amide, gamma—Butyrobetaine Amide and the Conglomerate from D- and L-Carnitine Amide," Advanced Synthesis & Catalysis, Wiley VCH Verlag, Weinheim, DE, vol. 322, No. 5, pp. 785-792.
Supplementary European Search Report from EP 07831967, dated Oct. 24, 2012.

\* cited by examiner

*Primary Examiner* — Sandra Saucier
(74) *Attorney, Agent, or Firm* — McDermott Will & Emery LLP

(57) ABSTRACT

According to the present invention, by using 4-halogeno-3-hydroxybutanamide as a substrate in quaternary amination reaction with trialkylamine which is an important step in betaine (such as carnitine) preparation processes, it becomes possible to reduce the production of crotonic acid derivatives (the major by-product) greatly compared to conventional processes. Consequently, it becomes possible to prepare a betaine, such as carnitine, at a high yield.

13 Claims, No Drawings

PROCESS FOR PRODUCTION OF A BETAINE SUCH AS CARNITINE

CROSS-REFERENCE TO PRIOR APPLICATION

This is the U.S. National Phase Application under 35 U.S.C. §371 of International Patent Application No. PCT/JP2007072237 filed Nov. 9, 2007, which claims the benefit of Japanese Patent Application No. 2006-303972 filed Nov. 9, 2006, both of them are incorporated by reference herein. The International Application was published in Japanese on May 15, 2008 as WO 2008/056827 A1 under pct article 21(2).

TECHNICAL FIELD

The present invention relates to a process for preparing betaine, especially carnitine.

BACKGROUND ART

L-Carnitine, a type of betaine, which is also known as vitamin BT, is an important compound involved in in vivo fatty acid metabolism. L-Carnitine has also attracted attention as a therapeutic for cardiac diseases (Japanese Unexamined Patent Publication No. S54-76830), as a therapeutic for hyperlipemia (Japanese Unexamined Patent Publication No. S54-113409) and as a therapeutic for venous diseases (Japanese Unexamined Patent Publication No. S58-88312).

As processes for preparing carnitine, a type of betaine, a number of processes have been reported. For example, Japanese Unexamined Patent Publication No. S57-165352 discloses a process in which L-carnitine is obtained from D-mannitol as the starting material; Japanese Unexamined Patent Publication No. S62-272983 discloses a process in which (R)-3,4-epoxybutyric acid ester is isolated selectively from (R,S)-3,4-epoxybutyric acid ester with an asymmetric hydrolase and then treated with trimethylamine or trimethylamine hydrochloride to thereby produce L-carnitine; Japanese Unexamined Patent Publication No. 2002-544252 discloses a process in which (S)-(−)-chlorosuccinic acid derivative is converted to a corresponding acid anhydride, which is then treated with trimethylamine to thereby produce L-carnitine; and Japanese Unexamined Patent Publication No. 2002-529528 discloses a process in which alkyl-4-chloro-3-oxobutylate is subjected to selective, asymmetric hydrogen reduction using a ruthenium complex catalyst to thereby produce alkyl-(R)-(+)-4-chloro-3-hydroxybutylate, which is then subjected to quaternary amination with trimethylamine to thereby obtain L-carnitine.

As seen from the disclosure in the above-listed patent documents, a step of introducing a quaternary amino group into the C4 skeleton using trimethylamine is an important step unavoidable in carnitine preparation. Besides, in many occasions, the yield at this step affects the total yield greatly. With respect to this quaternary amination, Japanese Unexamined Patent Publication No. H2-142758 discloses a process in which methyl 4-halogeno-3-hydroxybutyrate is quaternary aminated with trimethylamine in the presence of ketone solvent, and then the resultant butyric acid ester derivative is hydrolyzed. This quaternary amination is carried out in an autoclave at temperatures as high as 80° C. using alcohol as a solvent and anhydrous trimethylamine. Since olefin is produced as dehydration of methyl 4-halogeno-3-hydroxybutyrate proceeds, the selection ratio is remarkably low (about 30-40%) and the reaction time is rather long (20 hr or more). It is described that use of ketone solvent improves selectivity However, though the selectivity is greatly improved, the reaction time is still prolonged. Even 50 hr after the start of the reaction, the conversion ratio of methyl 4-halogeno-3-hydroxybutyrate is only about 80%. When ether or toluene is used as a solvent, the reaction time is further prolonged and the selection ratio does not rise considerably.

Japanese Patent Unexamined Publication No. H2-27995 discloses a process in which 30% aqueous solution of trimethylamine is added to γ-chloro-β-hydroxybutyronitrile and the resultant mixture is subjected to quaternary amination. The solid obtained by leaving the reaction solution at 4° C. overnight and then vacuum filtering has a yield of only about 75% even as carnitine nitrile chloride of 100% purity, which can not be said a high yield. Japanese Patent Unexamined Publication No. S60-258487 discloses a process in which largely excessive anhydrous trimethylamine is added to 4-chloro-3-hydroxybutyronitrile, and the resultant mixture is reacted without solvent in a 100° C. autoclave to thereby obtain carnitine nitrile chloride at a yield of 94%. The reaction conditions thereof are severe and the reaction time is rather long (24 hr).

On the other hand, as an example of reaction introducing an amino group not through quaternary amination, Japanese Examined Patent Publication No. 53-13611 discloses a process in which γ-chloro-β-hydroxybutylic acid amide is reacted with largely excessive (about 100 equivalents) ammonia at about 20° C. for 16 hr to thereby obtain γ-amino-β-hydroxybutylic acid amide. This process has two problems, i.e., use of largely excessive ammonia and the length of reaction time. A similar reaction is disclosed in Heterocycles, Vol. 53, No. 1, 2000. In this reaction, largely excessive (about 100 equivalents) aqueous ammonia is added to (S)-4-chloro-3-hydroxybutanamide and the resultant mixture is reacted in a tightly sealed system at 120° C. for 8 hr to thereby introduce an amino group. This reaction also has the problems of use of largely excessive ammonia and the length of reaction time.

As described above, it has been known that reacting 4-halogeno-3-hydroxybutyramide with largely excessive ammonia for a long time results in the introduction of an amino group. However, nothing has been known as to reacting with trialkylamine.

With respect to the step of quaternary amination with trialkylamine which greatly affects the total yield in betaine (such as carnitine) preparation processes, conventional quaternary amination of methyl 4-halogeno-3-hydroxybutylic acid or γ-chloro-β-hydroxybutyronitrile with trimethylamine is accompanied with progress of side reactions. Thus, it has been difficult to obtain a quaternary aminated product of interest at a high yield.

DISCLOSURE OF THE INVENTION

It is an object of the present invention to obtain betaine (such as carnitine) at a high yield by greatly preventing side reactions in the quaternary amination step important in betaine (such as carnitine) preparation processes.

As a result of intensive and extensive researches toward prevention of side reactions in the quaternary amination step of conventional carnitine preparation processes, the present inventors have succeeded in greatly reducing those side reactions which were occurring in the quaternary amination of butyronitrile or butyric acid ester with trialkylamine, by using 4-halogeno-3-hydroxybutyramide as a substrate for the amination reaction. When carnitine is prepared by using 4-halogeno-3-hydroxybutyramide as a substrate in the quaternary amination step of carnitine preparation process, it is possible to improve the yield greatly, to shorten the reaction time, and to inhibit side products greatly Further, this preparation process is applicable to not only carnitine but also specific types of betaine.

The present invention relates to the following matters.

(1) A process for preparing a 4-trialkylamino-3-hydroxybutyrnamide halide represented by formula (2') below:

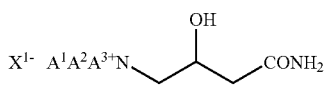
(2')

wherein $A^1$, $A^2$ and $A^3$ are independent from each other, may be the same or different, and individually represent a $C_1$-$C_{20}$ hydrocarbon group which may have a substituent(s), and $X^1$ is a halogen atom;
the process comprising a step of quaternary aminating 4-halogeno-3-hydroxybutyramide represented by formula (2) below:

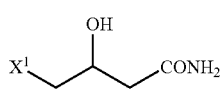
(2)

wherein $X^1$ is a halogen atom;
with a trialkylamine represented by ($NA^1A^2A^3$).

(2) The process according to (1) above, wherein the trialkylamine is selected from the group consisting of trimethylamine, triethylamine and tributylamine.

(3) A process for preparing a betaine represented by formula (1) below or a salt thereof:

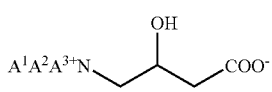
(1)

wherein $A^1$, $A^2$ and $A^3$ are independent from each other, may be the same or different, and individually represent a $C_1$-$C_{20}$ hydrocarbon group which may have a substituent(s);
the process comprising a step of hydrolyzing a halogenated 4-trialkylamino-3-hydroxybutanamide represented by formula (2') below:

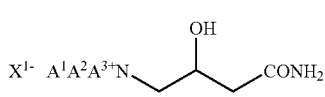
(2')

wherein $A^1$, $A^2$ and $A^3$ are independent from each other, may be the same or different, and individually represent a $C_1$-$C_{20}$ hydrocarbon group which may have a substituent(s), and $X^1$ is a halogen atom.

(4) The process according to (3) above, wherein $A^1$, $A^2$ and $A^3$ individually represent a methyl group.

(5) The process according to (3) or (4) above, wherein the 4-halogeno-3-hydroxybutyramide represented by formula (2) below:

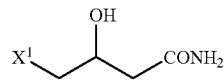
(2)

wherein $X^1$ is a halogen atom;
is obtained by a step of amidating 4-halo-3-hydroxybutyronitrile represented by formula (3) below:

(3)

wherein $X^1$ is a halogen atom.

(6) The process according to (5) above, wherein the amidation is performed with a nitrilehydratase.

(7) The process according to (6) above, wherein the nitrilehydratase is produced by a microorganism selected from the group consisting of microorganisms belonging to the genuses *Achromobacter, Acidovorax, Agrobacterium, Arthrobacter, Bacillus, Brevibacterium, Burkholderia, Candida, Caseobacter, Comamonas, Corynebacterium, Dietzia, Enterobacter, Erwinia, Geobacillus, Gordona, Klebsiela, Microascus, Morganella, Pantoea, Proteus, Pseudomonas, Pseudonocardia, Rhodococcus, Rhizobium, Serratia, Streptomyces, Syctalidium and Tukamurella.*

(8) The process according to any one of (5) to (7) above, wherein the step of preparing the 4-halogeno-3-hydroxybutyramide is performed at temperatures within a range from a temperature at which the reaction solution does not freeze to about 5° C.

(9) The process according to any one of (5) to (8) above, wherein the 4-halo-3-hydroxybutyronitrile represented by formula (3) below:

(3)

wherein $X^1$ is a halogen atom;
is obtained by a step of reacting an epihalohydrin represented by formula (4) below:

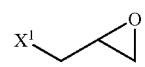
(4)

wherein $X^1$ is a halogen atom;
or 1,3-dihalo-2-propanol represented by formula (5) below:

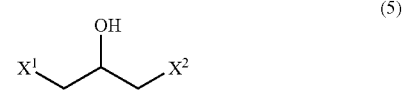
(5)

wherein $X^1$ is as defined above; and $X^2$ is independent from $X^1$ and represents an identical or different halogen atom;
with hydrogen cyanide or a cyanide salt.

(10) The process according to (9) above, wherein the reaction with hydrogen cyanide or a cyanide salt is performed in the presence of an enzyme catalyst.

(11) The process according to (10) above, wherein the enzyme catalyst is a halohydrin epoxidase.

(12) The process according to (11) above, wherein the 4-halo-3-hydroxybutyronitrile represented by formula (3) below:

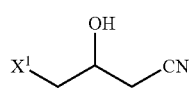

(3)

wherein $X^1$ is a halogen atom;
is produced in an (R)-isomer excessive manner.

(13) The process according to (11) or (12) above, wherein the halohydrin epoxidase is produced by a microorganism selected from the group consisting of microorganisms belonging to the genuses *Corynebacterium, Microbacterium, Agrobacterium, Mycobacterium* and *Arthrobacter*.

According to the present invention, by using 4-halogeno-3-hydroxybutanamide as a substrate in the quaternary amination with trialkylamine which is an important step in betaine (such as carnitine) preparation processes, it becomes possible to reduce the production of crotonic acid derivatives, the major by-product, greatly compared to conventional processes. Consequently, it becomes possible to prepare betaine, such as carnitine, at a high yield.

BEST MODE FOR CARRYING OUT THE INVENTION

Hereinbelow, embodiments of the present invention will be described. The embodiments described below are mere illustrations provided to explain the present invention, and it is not intended to limit the present invention to these embodiments. The present invention can be carried out in various embodiments without departure from the gist.

All publications cited herein (e.g., prior art documents and patent documents such as unexamined or examined patent publications) are incorporated herein by reference in their entirety. The present specification encompasses the contents of the specification of Japanese Patent Application No. 2006-303972 based on which the present patent application claims priority.

In the present invention, there is provided a process for preparing a 4-trialkylamino-3-hydroxybutyrnamide halide represented by formula (2') below:

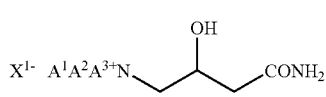

(2')

wherein $A^1$, $A^2$ and $A^3$ are independent from each other, may be the same or different, and individually represent a $C_1$-$C_{20}$ hydrocarbon group which may have a substituent(s), and $X^1$ is a halogen atom;

the process comprising a step of quaternary aminating 4-halogeno-3-hydroxybutyramide represented by formula (2) below:

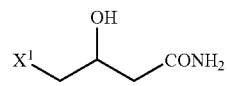

(2)

wherein $X^1$ is a halogen atom;

with a trialkylamine represented by ($NA^1A^2A^3$). The present invention also provides a process for preparing a betaine represented by formula (1) below or a salt thereof

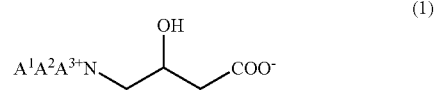

(1)

wherein $A^1$, $A^2$ and $A^3$ are independent from each other, may be the same or different, and individually represent a $C_1$-$C_{20}$ hydrocarbon group which may have a substituent(s);

the process comprising a step of hydrolyzing a halogenated 4-trialkylamino-3-hydroxybutanamide represented by formula (2') below:

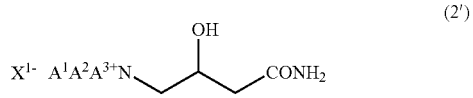

(2')

wherein $A^1$, $A^2$ and $A^3$ are independent from each other, may be the same or different, and individually represent a $C_1$-$C_{20}$ hydrocarbon group which may have a substituent(s), and $X^1$ is a halogen atom.

Further, the present invention provides a process for preparing a betaine represented by formula (1) below, comprising a step of quaternary aminating an amide represented by formula (2) below and a step of hydrolyzing the amide group:

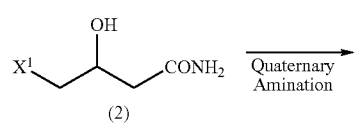

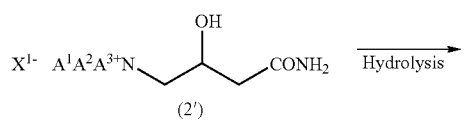

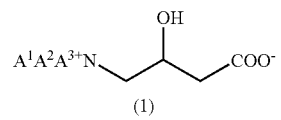

wherein $X^1$, A, $A^2$ and $A^3$ are as defined above.

The present invention provides a process for preparing a betaine represented by formula (1) below, comprising a step of quaternary aminating an amide represented by formula (2) below:

In the above formula, $A^1$, $A^2$ and $A^3$ are independent from each other, may be the same or different, and individually represent a $C_1$-$C_{20}$ hydrocarbon group which may have a substituent(s).

In the present specification, the hydrocarbon group of "$C_1$-$C_{20}$ hydrocarbon group" may be saturated or unsaturated acyclic, or saturated or unsaturated cyclic. When the $C_1$-$C_{20}$ hydrocarbon group is acyclic, the group may be linear or branched. The "$C_1$-$C_{20}$ hydrocarbon group" includes $C_1$-$C_{20}$ alkyl groups, $C_2$-$C_{20}$ alkenyl groups, $C_2$-$C_{20}$ alkynyl groups, $C_4$-$C_{20}$ alkyldienyl groups, $C_6$-$C_{18}$ aryl groups, $C_7$-$C_{20}$ alkylaryl groups, $C_7$-$C_{20}$ arylalkyl groups, $C_3$-$C_{20}$ cycloalkyl groups, $C_4$-$C_{20}$ cycloalkenyl groups and ($C_3$-$C_{10}$ cycloalkyl) $C_1$-$C_{10}$ alkyl groups.

In the present specification, "$C_1$-$C_{20}$ alkyl group" is preferably $C_1$-$C_{10}$ alkyl group, more preferably $C_1$-$C_6$ alkyl group. Examples of alkyl groups include, but are not limited to, methyl, ethyl, propyl, isopropyl, n-butyl, sec-butyl, tert-butyl, pentyl, hexyl and dodecanyl.

In the present specification, "$C_2$-$C_{20}$ alkenyl group" is preferably $C_2$-$C_{10}$ alkenyl group, more preferably $C_2$-$C_6$ alkenyl group. Examples of alkenyl groups include, but are not limited to, vinyl, 1-propenyl, 2-propenyl, isopropenyl and 2-butenyl.

In the present specification, "$C_2$-$C_{20}$ alkynyl group" is preferably $C_2$-$C_{10}$ alkynyl group, more preferably $C_2$-$C_6$ alkynyl group. Examples of alkynyl groups include, but are not limited to, ethynyl, propynyl and butynyl.

In the present specification, "$C_4$-$C_{20}$ alkyldienyl group" is preferably $C_4$-$C_{10}$ alkyldienyl group, more preferably $C_4$-$C_6$ alkyldienyl group. Examples of alkyldienyl groups include, but are not limited to, 1,3-butadienyl.

In the present specification, "$C_6$-$C_{18}$ aryl group" is preferably $C_6$-$C_{12}$ aryl group. Examples of aryl groups include, but are not limited to, phenyl, 1-naphtyl, 2-naphtyl, indenyl, biphenylyl, anthryl and phenanthryl.

In the present specification, "$C_7$-$C_{20}$ alkylaryl group" is preferably $C_7$-$C_{12}$ alkylaryl group. Examples of alkylaryl groups include, but are not limited to, o-tolyl, m-tolyl, p-tolyl, 2,3-xylyl, 2,4-xylyl, 2,5-xylyl, o-cumenyl, m-cumenyl, p-cumenyl and mesityl.

In the present specification, "$C_7$-$C_{20}$ arylalkyl group" is preferably $C_7$-$C_{12}$ arylalkyl group. Examples of arylalkyl groups include, but are not limited to, benzyl, phenetyl, diphenylmethyl, triphenylmethyl, 1-naphthylmethyl, 2-naphthylmethyl, 2,2-diphenylethyl, 3-phenylpropyl, 4-phenylbutyl and 5-phenylpentyl.

In the present specification, "$C_3$-$C_{20}$ cycloalkyl group" is preferably $C_3$-$C_{10}$ cycloalkyl group. Examples of cycloalkyl groups include, but are not limited to, cyclopropyl, cyclobutyl, cyclopentyl and cyclohexyl.

In the present specification, "$C_4$-$C_{20}$ cycloalkenyl group" is preferably $C_4$-$C_{10}$ cycloalkenyl group. Examples of cycloalkenyl groups include, but are not limited to, cyclopropenyl, cyclobutenyl, cyclopentenyl and cyclohexenyl.

In the present specification, the "$C_1$-$C_{20}$ hydrocarbon group" represented by each of $A^1$, $A^2$ and $A^3$ may have a substituent(s) introduced thereinto. Examples of this substituent include $C_1$-$C_{10}$ alkoxy groups (such as methoxy, ethoxy, propoxy or butoxy), $C_6$-$C_{12}$ aryloxy groups (such as phenyloxy, naphtyloxy or biphenyloxy), amino group, hydroxyl group, halogen atoms (such as fluorine, chloride, bromine or iodine) and silyl group. It should be noted that one or more substituents may be introduced at positions capable of substitution. Preferably, 1 to 4 substituents may be introduced. When the number of substituents is 2 or more, individual substituents may be the same or different.

In the present specification, $A^1$, $A^2$ and $A^3$ are independent from each other, may be the same or different, and each represent preferably a $C_1$-$C_{20}$ alkyl group, $C_3$-$C_{20}$ cycloalkyl group or $C_6$-$C_{18}$ aryl group, more preferably a $C_1$-$C_{10}$ alkyl group, $C_3$-$C_{10}$ cycloalkyl group or $C_6$-$C_{12}$ aryl group. Among all, methyl group is especially preferable because methyl group is led to carnitine that is an important compound involved in in vivo fatty acid metabolism.

In the present specification, the salt of betaine refers to salts formed between betaine and mineral acids such as hydrochloric acid, sulfuric acid and nitric acid; salts formed between betaine and organic acid such as fumaric acid and tartaric acid; salts formed between betaine and bases such as sodium hydroxide and potassium hydroxide; and the like. Specific examples of these salts include carnitine hydrochloride, carnitine fumarate and carnitine tartrate.

In the above-described formulas, $X^1$ represents a halogen atom, which may be fluorine, chloride, bromine or iodine. From the viewpoint of availability, chloride or bromine is more preferable.

The 4-halo-3-hydroxybutyronitrile represented by formula (3) above, the epihalohydrin represented by formula (4) above, the 4-halogeno-3-hydroxybutyramide represented by formula (2) above, the 4-trialkylamino-3-hydroxybutyrnamide halide represented by formula (2') above and the betaine represented by formula (1) above have asymmetric carbon atoms. The present invention may be performed in either racemic or optically active forms. Further, since the reaction according to the present invention may be carried out under moderate conditions, it is possible to pursue reactions up to the final product betaine without decreasing optical purity, even when optically active materials such as listed above were used or individual reactions were carried out after preparation of an optically active compound.

In the present invention, the "aqueous solvent" refers to water or a mixture of water and organic solvent. Water and organic solvent may be in a two-phase system. The organic solvent to be used is not particularly limited. For example, alcohol solvents such as methanol, ethanol, propanol, isopropanol and butanol; ketone solvents such as acetone and methylisobutylketone; ester solvents such as ethyl acetate, ethyl propionate and methyl methacrylate; hydrocarbon solvents such as pentane, hexane and heptane; aromatic solvents such as benzene, toluene and xylene; chlorine solvents such as dichloromethane and chloroform; acetonitrile; dimethylformamide; tetrahydrofuran; dimethylsulfoxide and the like may be enumerated. A mixture of these solvent may also be used. Use of an alcohol solvent highly soluble in water, acetonitrile, dimethylformamide or dimethylsulfoxide may be preferred. It is preferable to use the organic solvent within an amount that can be dissolved in water. Since a large amount of water accelerates reaction speed, use of water alone is especially preferred.

The preparation process of the present invention comprises a step of going through 4-halogeno-3-hydroxybutyramide represented by formula (2) below. The expression "going through" used herein means either (i) the amide represented by formula (2) below is used as a starting material; or (ii)

although other substance is used as a starting material, it goes through the amide represented by formula (2) below as an intermediate.

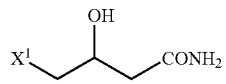
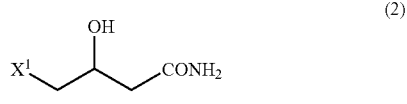
(2)

wherein $X^1$ is as defined above.

In the betaine preparation process of the present invention, it is preferable to use 4-halogeno-3-hydroxybutyramide as a substrate for quaternary amination. The process of the present invention is capable of greatly improving the yield of quaternary aminated product and greatly reducing by-products, compared to conventional processes.

The process for preparing 4-halogeno-3-hydroxybutyramide represented by formula (2) above is not particularly limited. For example, the following processes by chemical reaction may be enumerated: conversion to the amide using ester and ammonia; conversion to the amide using acid halide and ammonia; or conversion of nitrile to the amide using acid or base as a catalyst. Any of these processes may be used. As the process of conversion of nitrile to the amide, the following methods are known and any of them may be used: a method in which a mineral acid (such as hydrochloric acid) or formic acid is used; a method in which nitrile is treated with peroxide and alkali; or a method in which manganese dioxide is used.

It is also possible to prepare 4-halogeno-3-hydroxybutyramide represented by formula (2) above by amidating 4-halo-3-hydroxybutyronitrile represented by formula (3) above with the effect of a nitrilehydratase. Since this reaction can be performed under moderate conditions, it is possible to inhibit the progress of side-reactions which will occur in reactions using acid/base catalysts which need severe conditions and complicated operations.

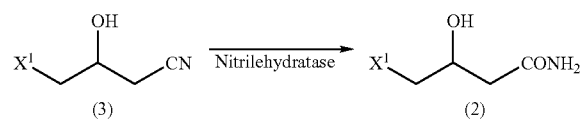

wherein $X^1$ is as defined above.

When 4-halo-3-hydroxybutyronitrile represented by formula (3) above is treated with a nitrilehydratase, further hydrolysis from the amide represented by formula (2) above does not occur. The amide represented by formula (2) above can be obtained under moderate conditions and yet in an almost quantitative manner.

In the present invention, the process for preparing 4-halo-3-hydroxybutyronitrile, a precursor of the amide represented by formula (2) above, is not particularly limited. For example, the following methods may be enumerated: a method of synthesis from an epihalohydrin represented by formula (4) below and hydrogen cyanide (disclosed in Japanese Unexamined Patent Publication No. 2002-241357); a method of synthesis from the epihalohydrin and cyanide salt (see Japanese Unexamined Patent Publication No. 2004-182607):

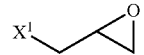
(4)

wherein $X^1$ is as defined above;
and a method of synthesis from 1,3-dichloro-2-propanol represented by formula (5) below and hydrogen cyanide (see Japanese Unexamined Patent Publication No. H5-219965):

(5)

wherein $X^1$ is as defined above; and $X^2$ is independent from $X^1$ and represents an identical or different halogen atom.

The precursor synthesized by any of these methods may be used. As the cyanide salt, alkali metal salts of hydrogen cyanide are preferable. More preferably, NaCN, KCN or LiCN is used. Further, when an optically active form of the epihalohydrin represented by formula (4) above is used, it is possible to prepare an optically active 4-halo-3-hydroxybutyronitrile.

Further, by using an enzyme catalyst (halohydrin epoxidase), an optically active 4-halo-3-hydroxybutyronitrile may be prepared directly from the epihalohydrin represented by formula (4) above or the 1,3-dihalo-2-propanol represented by formula (5) above.

In the present invention, the halohydrin epoxidase is not particularly limited as long as it has a function of producing 4-halo-3-hydroxybutyronitrile from the epihalohydrin represented by formula (4) above or the 1,3-dihalo-2-propanol represented by formula (5) above.

Examples of microorganisms producing halohydrin epoxidase include those microorganisms belonging to the genuses *Corynebacterium, Microbacterium, Agrobacterium, Mycobacterium* and *Arthrobacter*.

Specific examples of such microorganisms include *Corynebacterium* sp.N-1074 (FERM BP-2643), *Microbacterium* sp.N-4701 (FERM BP-2644), *Agrobacterium radiobacter* AD1, *Mycobacterium* sp. GP1 and *Arthrobacter* sp.AD2.

Especially preferable microorganisms are *Corynebacterium* sp.N-1074 (FERM BP-2643) and *Microbacterium* sp.N-4701 (FERM BP-2644). N-4701 strain was deposited at International Patent Organism Depositary, National Institute of Advanced Industrial Science and Technology (Tsukuba Central 6, 1-1-1 Higashi, Tsukuba City, Ibaraki, Japan) on Apr. 19, 1989, and their accession numbers are FERM BP-2643 and FERM BP-2644.

Further, those microorganisms into which a halohydrin epoxidase gene cloned from any of the above-listed microorganisms has been transformed are also included in the above-described halohydrin epoxidase-producing microorganism.

Halohydrin epoxidase genes are disclosed, for example, in GenBank. The accession number of the halohydrin epoxidase gene derived from *Corynebacterium* sp.N-1074 (hheB) is D90350.

The halohydrin epoxidase pertaining to the present invention may be obtained by culturing a microorganism with halohydrin epoxidase activity that is prepared as described above and collecting halohydrin epoxidase from the resultant culture.

As the medium for culturing such a microorganism with halohydrin epoxidase activity, either a natural medium or a synthetic medium may be used as long as the medium contains carbon sources, nitrogen sources and inorganic salts assimilable to the microorganism and is capable of culturing transformants efficiently Examples of carbon sources include hydrocarbons such as glucose, fructose, sucrose and starch; organic acids such as acetic acid and propionic acid; and alcohols such as ethanol and propanol. Nitrogen sources include ammonia; ammonium salts of organic or inorganic acid such as ammonium chloride, ammonium sulfate, ammonium acetate and ammonium phosphate; other nitrogen-containing compounds; peptone; meat extract; corn steep liquor; and the like. Inorganic materials include potassium dihydrogenphosphate, dipotassium hydrogenphosphate, magnesium phosphate, magnesium sulfate, sodium chloride, iron(II) sulfate, manganese sulfate, copper sulfate and calcium carbonate.

The above-described microorganism may be cultured by conventional methods. For example, the microorganism is cultured aerobically at pH 4-10 and at 10-45° C. for 10-180 hr. The culture may be either liquid culture or solid culture. Preferably, transformants are cultured under aerobic conditions (such as shaking culture or aeration-agitation culture) at 30-40° C. If necessary, antibiotics (such as ampicillin or kanamycin) or inducers may be added to the medium during culturing.

The culture (or a treated material thereof) obtained by culturing a halohydrin epoxidase producing microorganism prepared as described above is capable of producing 4-halo-3-hydroxybutyronitrile from the epihalohydrin represented by formula (4) above or the 1,3-dihalo-2-propanol represented by formula (5). The term "treated material" means disrupted cells, cells treated with drugs, immobilized cells, or cell extracts such as crude enzyme or purified enzyme.

The solvent for reaction is not particularly limited. Generally, the above-described aqueous solvent is used. Water is especially preferable. Water or buffer whose pH is around the optimum pH (4-10) for the enzyme activity is used. Examples of preferable buffers include those buffers composed of salts of phosphoric acid, boric acid, citric acid, glutaric acid, malic acid, malonic acid, o-phthalic acid, succinic acid or acetic acid; Tris buffer and Good's buffer.

The reaction is performed preferably at 5-50° C. within a pH range of 4 to 10. The reaction temperature is more preferably 10-40° C. The pH range is more preferably from 6 to 9. The reaction time may be selected appropriately depending on the concentration of substrate, etc., the cell concentration or other reaction conditions etc. It is preferable to set conditions so that the reaction will be completed in 1-120 hr. As the reaction proceeds, chloride ions are generated. By neutralizing these ions with an appropriate alkali, it is possible to pursue the reaction more smoothly.

As a cyano compound, hydrogen cyanide, potassium cyanide, sodium cyanide, cyanic acid, or a compound such as acetone cyanohydrin which produces cyanide ion (CN—) or hydrogen cyanide when added to the reaction solution, or a solution of such a compound may be used.

The substrate concentration in the reaction solution is preferably 0.01-20 (w/v) %, especially preferably 0.01-10% from the viewpoint of enzyme stability.

The amount of cyano compound used is preferably 1-3 fold (mole) of the amount of substrate.

The 4-halo-3-hydroxybutyronitrile of formula (3) above prepared in the above-described method may be collected and purified by known methods. For example, after cells are removed from the reaction solution by a method such as centrifugation, the resultant solution is extracted with a solvent such as ethyl acetate. Removal of the solvent under reduced pressure yields a syrup of 4-halo-3-hydroxybutyronitrile. Frequently, coloring occurs to give the reaction solution a brown color. Decoloring operation may be performed with active carbon or the like. The resultant syrup may be purified further by vacuum distillation.

When the present invention is practiced using an optically active 4-halo-3-hydroxybutyronitrile, it is possible to pursue reactions up to betaine without decreasing the initial optical purity because subsequent reactions are performed under moderate conditions.

In the present invention, nitrilehydratase is not particularly limited, but it is an enzyme which catalyzes the reaction of converting the nitrile in 4-halo-3-hydroxybutyronitrile of formula (3) above into an amide and which is classified as lyase according to the international enzyme classification. Examples of microorganisms having the nitrilehydratase used in the present invention include microorganisms belonging to the genuses *Achromobacter, Acidovorax, Agrobacterium, Arthrobacter, Bacillus, Brevibacterium, Burkholderia, Candida, Caseobacter, Comamonas, Corynebacterium, Dietzia, Enterobacter, Erwinia, Geobacillus, Gordona, Klebsiela, Microascus, Morganella, Pantoea, Proteus, Pseudomonas, Pseudonocardia, Rhodococcus, Rhizobium, Serratia, Streptomyces, Syctalidium* and *Tukamurella*.

Specific examples of the nitrilehydratase used in the present invention include those nitrilehydratases produced by *Arthrobacter globi-formis* IFO 12138, *Brevibacterium helvolum* ATCC 11822, *Corynebacterium flaves-cens* IAM 1642, *Rhodococcus erythropolis* IFO 12540 and IFO 12539, *Streptomyces albogriseolus* HUT 6045, *Streptomyces chrysomallus* HUT 6141, *Streptomyces cinereouruber* HUT6142, *Streptomyces diastaticus* HUT 6116, *Streptomyces olivaceus* HUT 6061, *Streptomyces rubrocyanodiastaticus* HUT 6117, *Klebsiella pneumoniae* IFO 12019, IFO 3319, IFO12059 and IAM 1063, *Klebsiella pneumoniae* subsp. *pneumoniae* NH-36T2 strain, *Serratia plymuthica* IFO 3055, *Serratia marcescens* IAM 1105, *Erwinia carotovora* IFO 3057, *Tukamurella paurometabolum* JCM 3226, *Gordona rubropertinctus* JCM 3227, *Morganella morganii* IFO 3848, *Proteus vulgaris* IFO 3167, *Enterobacter aerogenes* IFO 12010, *Microascus desmosporus* IFO6761, *Candida guilliermondii* NH-2 strain (FERM P-11350) and *Pantoea agglomerans* NH-3 strain (FERM P-11349).

Microorganism strains with ATCC number are easily available from the American Type Culture Collection (ATCC). Microorganisms with IFO number are listed in the List of Cultures, 8th edition, vol. 1 (1988) published by Institute for Fermentation, Osaka (IFO) and currently available from Resource Collection Division, NITE Biological Resource Center (NBRC), Department of Biotechnology, National Institute of Technology and Evaluation (NITE), Japan. Microorganisms with LAM number are available from the Institute of Molecular and Cellular Biosciences, the University of Tokyo. Microorganisms with JCM number are listed in the Catalogue of Strains, 4th edition (1989) published by Japan Collection of Microorganisms, RIKEN and available from the same Collection. Microorganisms with HUT number are listed in the Catalogue of Cultures, 4th edition (1987) published by Japanese Federation of Culture Collections of Microorganisms (JFCC) and available from the Engineering Department, Hiroshima University. Microorganisms with FERM number are available from International Patent Organism Depositary, National Institute of Advanced Industrial Science and Technology.

Additional examples of the nitrilehydratase used in the present invention include those nitrilehydratases produced by the following microorganisms isolated by Yamada et al. from soil: *Rhodococcus rhodochrous* J-1 (FERM BP-1478), *Arthrobacter* sp. SK103 (FERM P-11300), *Caseobacter* sp. BC23 (FERM P-11261), *Pseudomonas* sp. BC15-2 (FERM BP-3320), *Pseudomonas* sp. SK31 (FERM P-11310), *Pseudomonas* sp. SK87 (FERM P-11311), *Pseudomonas* sp. SK13 (FERM BP-3325), *Rhodococcus* sp. SK70 (FERM P-11304), *Rhodococcus* sp. HR11 (FERM P-11306) and *Rhodococcus* sp. SK49 (FERM P-11303). These microorganisms are deposited at International Patent Organism Depositary, National Institute of Advanced Industrial Science and Technology with the respective accession numbers indicated above.

Further, microorganisms into which a nitrilehydratase gene cloned from any of the above-listed microorganisms has been transformed are also included in the above-described nitrilehydratase-producing microorganism. Specific examples of such microorganisms include *Escherichia coli* MT-10822 strain (FERM BP-5785) transformed with *Pseudonocardia*-derived nitrilehydratase gene disclosed in U.S. Pat. No. 5,807,730; *Escherichia coli* MT-10770 strain (FERM P-14756) transformed with *Achromobacter*-derived nitrilehydratase gene disclosed in Japanese Unexamined Patent Publication No. H8-266277; and a microorganism transformed with *Rhodococcus rhodochrous*-derived nitrilehydratase gene disclosed in Japanese Unexamined Patent Publication No. H4-211379.

The composition of the medium for culturing a microorganism producing the nitrilehydratase to be used in the present invention is not particularly limited. Usually, any medium may be used as long as the microorganism can grow therein. For example, as carbon sources, saccharides such as glucose, fructose, sucrose and maltose; organic acids such as acetic acid and citric acid; and alcohols such as ethanol and glycerol may be used. As nitrogen sources, natural nitrogen sources such as peptone, meat extract, yeast extract, protein hydrolysate and amino acids; and various ammonium salts of inorganic and organic acids may be used. Further, inorganic salts, trace metals, vitamins or the like may be used appropriately, if necessary. In order to induce still higher enzyme activity, addition of various nitrile compounds (such as 4-chloro-3-hydroxybutyronitrile, propionitrile, isobutyronitrile, benzylcyanide, etc.) and various amide compounds (4-chloro-3-hydroxybutanamide, propionamide, isobutanamide, etc.) to the medium is more preferable. The above-described microorganism may be cultured according to conventional methods. For example, the microorganism is cultured aerobically at pH 4-10 at 10-45° C. for 10-180 hr. The culture may be performed by either liquid culture or solid culture.

In the present invention, the process of obtaining 4-halogeno-3-hydroxybutyramide by reacting 4-halo-3-hydroxybutyronitrile with an enzyme is not particularly limited. For example, any of the following processes may be used: a process in which the substrate is added to the culture broth of a nitrilehydratase-producing microorganism obtained as described above, or to a suspension of microorganism cells obtained by a method such as centrifugation; a process in which the substrate is added to a suspension of a treated material of the microorganism cell (e.g., disrupted cells, cell extracts, or the like), nitrilehydratase crude enzyme or purified enzyme; or a process in which conventionally immobilized cells or treated material of cells, crude enzyme or purified enzyme is added to the reaction solution; a process in which the substrate is added to the culture broth at the time of culture of the microorganism, to thereby perform the reaction simultaneously with culturing; or a process in which an aqueous solution of the substrate is prepared, and into the resultant solution, the microorganism culture broth, microorganism cells, treated material of microorganism cells, nitrilehydratase crude enzyme or purified enzyme obtained as described above and may be immobilized is added as a whole or in portions. Since this amidation reaction is an exothermic reaction, it is preferred for prevention of the uncontrolled run of the reaction caused by generated heat that a cell suspension should be added to an aqueous solution of the substrate to control the reaction rate.

The amidation reaction with nitrilehydratase may also be performed using the reaction solution as it is when synthesis of 4-halo-3-hydroxybutyronitrile by reacting epihalohydrin or 1,3-dichloro-2-propanol with hydrogen cyanide or a cyanide salt has been completed therein. In this case, cyanide compounds remaining in the system often deactivate nitrilehydratase. For prevention of such deactivation, it is preferable to decrease the cyanide concentration in the system to 10 ppm or less, more preferably 1 ppm or less, by performing in advance such operations as heating, vacuuming and topping under acidic conditions.

When the amidation of 4-halo-3-hydroxybutyronitrile does not proceed promptly even the cyanide concentration in the system has been lowered to 1 ppm or less, heating 4-halo-3-hydroxybutyronitrile or solution thereof can progress the amidation promptly.

The method of heating is not particularly limited as long as the object of the present invention is achieved. This heating may be performed under pressure, vacuum or ambient pressure. For example, a method may be given in which 4-halo-3-hydroxybutyronitrile and solution thereof are heated exceeding their boiling point, and then refluxed or distilled. The solution may be either organic solution or aqueous solution, or a mixture thereof. However, usually, amidation reaction is performed in water as a solvent and continuous reaction is possible therein. Therefore, it is preferable to carry out the heating treatment in water as a solvent.

The heating time is about 0.1-100 hr, preferably 0.5-50 hr, more preferably 1-10 hr. The heating temperature may be within a range from about 40° C. to a temperature at which 4-halo-3-hydroxybutyronitrile is not degraded, preferably within a range from 60 to 150° C. When aqueous solution of 4-halo-3-hydroxybutyronitrile is heated, the pH is preferably in a range from neutral to acidic, more preferably in a range from 1 to 7, for preventing its degradation.

It is also possible to pursue the amidation reaction promptly by adding a trace amount of metal salt to convert the cyanide ion contained in an extremely trace amount in 4-halo-3-hydroxybutyronitrile to a metal complex, to thereby reduce the cyanide ion. The method of conversion to a metal complex is a method in which, before contacting the nitrile with nitrilehydratase, a metal that forms metal cyanide complex upon reaction with hydrogen cyanide is added as a metal salt to the nitrile or the nitrile-containing solution, to thereby convert the cyanide ion to a metal cyanide complex. As the metal, cobalt, nickel or zinc is preferable. The form of the salt is not particularly limited. For example, nitrate, chloride, sulfate, carboxylate or the like may be enumerated. Alternatively, a hydrate may be used.

When a trace amount of metal salt is added, the amount must correspond to the concentration of cyanide ion contained in the 4-halo-3-hydroxybutyronitrile-containing solution. When the amount of metal salt added is insufficient, it is impossible to eliminate the effect of cyanide ion sufficiently When the amount added is excessive, the metal salt is likely to inhibit the amidation reaction. After the addition of a metal salt, it is preferable to re-adjust the pH of the reaction solution to the optimum pH at which nitrilehydratase exhibits high activity, before proceeding to amidation reaction.

The conditions for the amidation reaction with nitrilehydratase in the present invention are not particularly limited. The reaction temperature is selected appropriately depending on the enzyme to be used. Generally, the reaction temperature is in a range from a temperature at which the reaction solution does not freeze to about 50° C. The "temperature at which the reaction solution does not freeze" varies depending on the solution in which amidation is performed. If the amidation is performed in a dilute solution, the temperature may be calculated from the mole concentration (mol/kg) of the solute dissolved in the reaction solution and the molar depression of freezing point of the solvent. For example, when about 14% 4-halo-3-hydroxybutyronitrile dissolved in aqueous solvent is used in the amidation reaction, the freezing point will be around −2° C. since the molar depression of freezing point in water is 1.858 and the mole concentration (mol/kg) of 4-halo-3-hydroxybutyronitrile is 1.171. Japanese Patent No. 3014171 discloses that the reaction temperature for synthesizing 4-halogeno-3-hydroxybutyramide by reacting 4-halo-3-hydroxybutyronitrile with an enzyme is 5-50° C. In the present invention, the amidation of 4-halo-3-hydroxybutyronitrile to 4-halogeno-3-hydroxybutyramide especially for the purpose of preparing betaine is performed more preferably at temperatures within a range from a temperature at which the reaction solution does not freeze to about 30° C., particularly preferably within a range from a temperature at which the reaction solution does not freeze to about 5° C., in order to inhibit the progress of side reactions. The concentration of 4-halo-3-hydroxybutyronitrile is not particularly limited. The concentration is usually about 0.01-50 (w/v) %, preferably about 0.1-40%. The pH of the reaction solution is preferably in a range from 4 to 10, more preferably in a range from 6 to 9. The reaction time varies depending on the substrate concentration, cell concentration or other reaction conditions. Preferably, the reaction conditions are set so that the reaction is completed in 0.5-120 hr. For inhibiting the progress of side reactions, it is more preferable to set the conditions so that the reaction is completed in about 0.5-24 hr, more preferably in about 0.5-15 hr.

The 4-halogeno-3-hydroxybutyramide synthesized as described above may be isolated and purified by conventional methods such as extraction, column separation, re-crystallization, etc. When a microorganism having nitrilehydratase was used, cells may be filtered after the completion of reaction. However, since 4-halogeno-3-hydroxybutyramide is unstable in aqueous solution, the filtering operation be performed at low temperatures. Preferably, the operation is performed at about 0-10° C.

When optically active 4-halo-3-hydroxybutyronitrile was used as the substrate for amidation, the resultant 4-halogeno-3-hydroxybutyramide is also optically active. When either one of the isomers is excessive, the optical purity may be improved by, for example, re-crystallization of 4-halogeno-3-hydroxybutyramide. When racemic 4-halogeno-3-hydroxybutyramide was prepared, it is possible to obtain optically active 4-halogeno-3-hydroxybutyramide using optical resolution agents or the like.

The 4-halogeno-3-hydroxybutyramide of formula (2) above used in the present invention may be either in a purified form or in the state of aqueous solution after treatment with nitrilehydratase. However, as stated above, 4-halogeno-3-hydroxybutyramide is unstable in aqueous solution and, when subjected to isolation and purification, may cause further reactions to thereby decrease the yield. Taking into account of this point, the complexity of column purification and rather low isolation/purification yield (about 80%) obtained thereby, and the total yield up to the final product, it is preferable to use the nitrilehydratase-treated aqueous solution as it is.

Since 4-halogeno-3-hydroxybutyramide is unstable in aqueous solution as described above, it is more preferable to shift to the quaternary amination reaction with trialkylamine within 48 hr, especially preferably 10 hr. after completion of the preparation of 4-halogeno-3-hydroxybutanamide, for inhibiting side reactions. It is also preferable that the temperature of the reaction solution containing 4-halogeno-3-hydroxybutanamide should be kept at 0-10° C. until contact with trialkylamine.

In the present invention, the process of preparing the betaine represented by formula (1) below preferably comprises a step of quaternary aminating the amide represented by formula (2) below and a step of hydrolyzing the amide group. Since the hydrolysis reaction of compound (2) is accompanied by various side reactions, 4-trialkylamino-3-hydroxybutyrnamide halide shown in formula (2') below is prepared by quaternary amination in advance and then hydrolysis step is performed, from the viewpoint of improvement of yield.

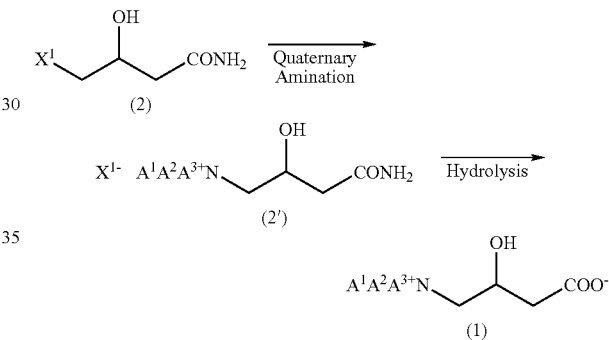

wherein $X^1$, $A^1$, $A^2$ and $A^3$ are as defined above.

In the present invention, it is preferable to use a trialkylamine ($NA^1A^2A^3$) such as trimethylamine, triethylamine or tributylamine in the step of quaternary aminating the amide represented by formula (2) above. The trialkylamine used in the present invention may be either anhydrous or in the state of aqueous solution.

When the quaternary amination reaction is performed using a solution of 4-halogeno-3-hydroxybutanamide represented by formula (2) above, the solvent is not particularly limited. Preferably, the above-listed aqueous solvents are used.

When the quaternary amination reaction is performed using a solution of 4-halogeno-3-hydroxybutanamide represented by formula (2) above, the trialkylamine used in this reaction may be either an anhydrous trialkylamine or an aqueous solution thereof. However, when an organic solvent compatible with water is used as a solvent for 4-halogeno-3-hydroxybutanamide, use of an aqueous trialkylamine solution is more preferable since it often results in high yield and high reaction rate. Further, it is especially preferable to use an aqueous solution of 4-halogeno-3-hydroxybutyramide or the aqueous solution as it is which completed the synthesis of 4-halogeno-3-hydroxybutyramide through treatment of 4-halo-3-hydroxybutyronitrile with nitrilehydratase, because use of water alone in the reaction results in still higher yield and higher reaction rate.

In the commencement of the quaternary amination reaction in an aqueous solvent, a trialkylamine may be added to 4-halogeno-3-hydroxybutyramide. Alternatively, 4-halogeno-3-hydroxybutyramide may be added to a trialkylamine. It is desirable to heat the reaction solution to a specific temperature after completion of the addition.

The concentration of 4-halogeno-3-hydroxybutyramide in the quaternary amination reaction is not particularly limited. The concentration is usually about 0.1-50%, preferably about 1-20%. The amount of trialkylamine used is not particularly limited. The amount is usually 1.0-20.0 equivalent moles, preferably about 1.1-8.0 equivalent moles, relative to the 4-halogeno-3-hydroxybutyramide. The reaction temperature is not particularly limited. Usually, the temperature is in the range from about −10° C. to 60° C., and preferably about 0° C. to 50° C.

When a trialkylamine with a low boiling point (such as trimethylamine) is used, it is preferable to pay attention at reduction of the trialkylamine by vaporization. Especially when the equivalent number of the trialkylamine used in the reaction is relatively low such as 1.2 equivalents or less against 4-halogeno-3-hydroxybutyramide, a remarkable difference is observed in the yield of 4-trialkylamino-3-hydroxybutyrnamide halide between cases where attention has been paid to prevent vaporization and where no attention has been paid.

In quaternary amination reaction, sometimes brown-coloration occurs. For decoloration, decoloring operation with active carbon or the like may be performed.

The 4-trialkylamino-3-hydroxybutyrnamide halide of formula (2') above synthesized as described above may be isolated and purified by conventional methods such as extraction, column separation, re-crystallization, electrodialysis, ion exchange, etc.

When optically active 4-halo-3-hydroxybutyronitrile or 4-halogeno-3-hydroxybutyramide was used as a precursor or a substrate in quaternary amination reaction, the 4-trialkylamino-3-hydroxybutyrnamide halide of formula (2') above will also be optically active. If one of the isomers is excessive, the optical purity of the 4-trialkylamino-3-hydroxybutyrnamide halide of formula (2') above can be improved by re-crystallization operation or the like. When a racemic form of 4-trialkylamino-3-hydroxybutyrnamide halide was prepared, it is possible to obtain optically active 4-trialkylamino-3-hydroxybutyrnamide halide using optical resolution agents or the like.

When quaternary amination reaction is performed in an aqueous solvent using 4-halogeno-3-hydroxybutyramide as a substrate, a quaternary aminated product is produced at a remarkably high yield, compared to previously reported quaternary amination reactions of 4-halo-3-hydroxybutyronitrile or 4-halo-3-hydroxybutyric acid ester. It is presumed that the major reaction of quaternary amination is as follows: after epoxy compound is generated from halohydrin compound via dehydrochloric acid reaction, a quaternary aminated product is generated by nucleophilic attack of trialkylamine. On the other hand, it is presumed that isomerization reaction to crotonic acid derivatives is the side reaction. Easy occurrence of this isomerization reaction to crotonic acid derivatives controls the yield of quaternary aminated product, and it is expected that what determines the easiness of isomerization is the electron withdrawal of functional groups. The electron withdrawal of amides is lower than that of functional groups such as nitrile or ester, and thus amides do not cause isomerization reaction to crotonic acid derivatives easily Therefore, it is presumed that the ratio of isomerization reaction from epoxy compound to crotonic acid derivatives decreased, which resulted in an increase in the ratio of nucleophilic attack of trialkylamine, leading to a rise in the yield of quaternary aminated product.

In the present invention, in a step of hydrolyzing the 4-trialkylamino-3-hydroxybutyrnamide halide of formula (2') above, the process of hydrolysis is not particularly limited. The step may be performed by various known processes using acid catalyst or base catalyst. For example, Japanese Examined Patent Publication No. S43-26849 and Japanese Unexamined Patent Publication No. S55-13299 disclose a process of hydrolysis using oxalic acid; Japanese Examined Patent Publication No. S43-26850 discloses a process of hydrolysis using n-butyl nitrite, glacial acetic acid and hydrochloric acid gas; Japanese Unexamined Patent Publication No. H1-287065 discloses a process of hydrolysis from carnitine nitrile chloride to nitrile→amide→carboxylic acid consistently using base catalysts such as alkali metal hydroxides or alkaline earth metal hydroxides. Japanese Unexamined Patent Publication No. H4-320679 discloses a process using an enzyme that converts carnitine amide to L-carnitine, wherein the enzyme is not limited to acid catalyst, base catalyst or enzyme catalyst.

The major by-product generated in hydrolysis reaction of 4-trialkylamino-3-hydroxybutyrnamide halide is crotonobetaine which is a dehydrated product.

In hydrolysis reaction of 4-trialkylamino-3-hydroxybutyrnamide halide using acid catalyst, it is possible to inhibit the generation of this crotonobetaine (to 0.1 wt % or less relative to betaine). However, strict reaction conditions are required because the reaction rate is low. Examples of acidic substances to be used for this purpose include mineral acids such as hydrochloric acid, sulfuric acid, phosphoric acid and nitric acid; and organic acids with a relatively small number of carbon atoms such as acetic acid and trifluoroacetic acid. Use of industrially commonly used hydrochloric acid or sulfuric acid is preferred.

In hydrolysis reaction of 4-trialkylamino-3-hydroxybutyrnamide halide using base catalyst, the yield of crotonobetaine is larger compared to the hydrolysis using acid catalyst. However, depending on the type of the base, it is possible to pursue the reaction even at room temperature. Under such moderate reaction conditions, inhibiting the production of crotonobetaine (to about 1 wt % or less relative to betaine) is also possible. Besides, in the case of reaction with base catalyst, it is also possible to vaporize and remove the byproduced ammonia, which leads to reduction of the salts byproduced in the neutralization after hydrolysis. Examples of basic substances to be used include alkali metal hydroxides, alkaline earth metal hydroxides, carbonates or bicarbonates of alkali metals, tertiary amines, quaternary ammonium hydroxide, and basic anion exchange resins. More specifically, NaOH, KOH, $Ca(OH)_2$, $Na_2CO_3$, $K_2CO_3$, triethylamine, $NH_4OH$ and anion exchange resin IRA-400 may be enumerated. These substances may be used alone or in combination. Especially preferable are NaOH and KOH which are capable of progressing reactions efficiently even below room temperature. Besides, the by-production of crotonobetaine is less when they are used.

The acid or base may be used to give an equimolar concentration or more against the 4-trialkylamino-3-hydroxybutyrnamide halide of formula (2') above; specifically, about 1.1-5.0 equivalents is preferable. The concentration of 4-trialkylamino-3-hydroxybutyrnamide halide of formula (2') above is not particularly limited. The concentration is usually about 1-50%, preferably about 5-30%. The reaction temperature is not particularly limited. Usually, 5-100° C. is preferable. Since production of crotonobetaine is extremely small when acid catalyst is used, 60-100° C. is especially preferable from the viewpoint of reaction time. Further, the results of intensive and extensive examination of the use of base catalyst revealed that the amount of crotonobetaine byproduced depends on reaction temperature, i.e., the lower the reaction temperature, the less the byproduction. Therefore, when base catalyst is used, the reaction temperature is preferably 10-60° C. from the viewpoint of inhibition of the crotonobetaine byproduction.

The solvent is not particularly limited. Preferably, the above-listed aqueous solvents are used. Use of water alone as a solvent is especially preferable from the viewpoints of reaction rate and inhibition of side reactions. When quaternary amination reaction was performed in an aqueous solvent, it is more preferred that the subsequent hydrolysis reaction be performed in that aqueous solvent as it is.

Any of the so far described amidation reaction of 4-halo-3-hydroxybutyronitrile, quaternary amination reaction of 4-halogeno-3-hydroxybutyramide and hydrolysis reaction of 4-trialkylamino-3-hydroxybutyrnamide halide is preferably performed in an aqueous solvent from the viewpoint of reaction rate. The effect becomes more remarkable when water alone is used as a reaction solvent. Further, usually, the synthesis of 4-halo-3-hydroxybutyronitrile from epihalohydrin or 1,3-dihalo-2-propanol is also performed in an aqueous solvent. Hence, use of water alone as a solvent in all of the above-described reactions is more preferable because that makes it possible to perform reactions from the starting material up to betaine in one pot.

Light brown-coloration sometimes occurs in hydrolysis reaction. Coloration can also occur after neutralization performed after completion of hydrolysis reaction. For decoloration, decoloring operation may be performed with active carbon or the like.

The betaine obtained as described above may be isolated and purified by conventional methods such as extraction, column separation, re-crystallization, electrodialysis, ion exchange, etc.

When an optically active form of 4-halo-3-hydroxybutyronitrile, 4-halogeno-3-hydroxybutyramide or 4-trialkylamino-3-hydroxybutyrnamide halide is used as a precursor or substrate in a hydrolysis reaction, the resultant betaine is also optically active. If one of the isomers is excessive, the optical purity of betaine may be improved by operations such as re-crystallization. When a racemic betaine was produced, it is possible to obtain an optically active betaine using optical resolution agents or the like.

Although it is possible to improve optical purity by re-crystallization, etc. at any of the stages of 4-halogeno-3-hydroxybutyramide, 4-trialkylamino-3-hydroxybutyrnamide halide and betaine, it is preferable to perform re-crystallization, etc. after the final product betaine has been produced, for purposes of both purification and improvement of optical purity, because by-products are generated in each reaction step.

In the present invention, when a betaine has been produced by preparing or using optically active epihalohydrin, 4-halo-3-hydroxybutyronitrile, 4-halogeno-3-hydroxybutyramide or 4-trialkylamino-3-hydroxybutyrnamide halide, it is possible to produce a corresponding, optically active betaine without reducing optical purity. That is, the present invention is useful as a process of producing an optically active betaine, in particular L-carnitine.

EXAMPLES

Hereinbelow, the present invention will be described with reference to the following Examples. However, the present invention is not limited to these Examples.

Details of analysis methods will be described below for the various quantitative determination analyses used in the present invention.

Analysis Method (1)
  Target Compounds for Analysis
    1,3-dichloro-2-propanol (hereinafter, abbreviated to "DCP")
    epichlorohydrin (hereinafter, abbreviated to "ECH")
    4-chloro-3-hydroxybutyronitrile (hereinafter, abbreviated to "CHBN")
  Sample Preparation Method: reaction solution is dissolved in mobile phase
  Column: Inertsil ODS-3V, 4.6 mm I.D.×250 mm, particle size 5 μm (GL Science)
  Column Oven Temperature: 40° C.
  Mobile Phase: water/acetonitrile/phosphoric acid=70/30/0.1, 1 mL/min
  Detector: Differential refractive index detector (RI)
  Sample Volume: 20 μl

| Retention Time: | DCP | 15.7 min |
|---|---|---|
| | ECH | 11 min |
| | CHBN | 7.2 min |

Analysis Method (2)
  Target Compounds for Analysis
    4-chloro-3-hydroxybutyronitrile (hereinafter, abbreviated to "CHBN")
    4-chloro-3-hydroxybutanamide (hereinafter, abbreviated to "CHBA")
    4-hydroxycrotonamide (hereinafter, abbreviated to "CHAm")
  Sample Preparation Method: reaction solution is dissolved in mobile phase
  Column: Inertsil ODS-3V, 4.6 mm I.D.×250 mm, particle size 5 μm (GL Science)
  Column Oven Temperature: 40° C.
  Mobile Phase: 0.05% aqueous trifluoroacetic solution, 1 mL/min
  Detector: Differential refractive index detector (JASCO Corporation Model RI-2031)
  Sample Volume: 20 μl

| Retention Time: | CHBN | 11.0 min |
|---|---|---|
| | CHBA | 6.7 min |
| | HCAm | 4.4 min |

Analysis Method (3)
  Target Compounds for Analysis
    carnitinamide chloride (hereinafter, abbreviated to "Car-amide")
    carnitinenitrile chloride (hereinafter, abbreviated to "Car-nitrile")
    carnitine (hereinafter, abbreviated to "Car")
  Sample Preparation Method: reaction solution is dissolved in mobile phase
  Column: Shodex IC YK-421, 4.6 mm I.D.×125 mm (GL Science)
  Column Oven Temperature: 40° C.
  Mobile Phase: 3 mM $HNO_3$ aq/ATN=4/6, 1 mL/min
  Detector: Electrical conductivity detector (Model CD-5; Shodex)
  Sample Volume: 20 μl

| Retention Time: | Car-amide | 10.2 min |
| --- | --- | --- |
| | Car-nitrile | 8.9 min |
| | Car | 7.9 min |

Analysis Method (4)

Target Compounds for Analysis carnitine (hereinafter, abbreviated to "Car")

crotonobetaine (hereinafter, abbreviated to "CB")

Sample Preparation Method: reaction solution is dissolved in mobile phase

Column: Nucleosil 100-5N(CH$_3$)$_2$, 4.6 mm I.D.×250 mm (GL Science)

Column Oven Temperature: 40° C.

Mobile Phase: 50 mM KH$_2$PO$_4$ (pH 4.7) aq/ATN=35/65, 1 mL/min

Detector: UV detector (205 nm) JASCO Corporation Model UV-930

Sample Volume: 5 μl

| Retention Time: | Car | 10.8 min |
| --- | --- | --- |
| | CB | 13.0 min |

Analysis Method (5)

Determination of the Optical Purity of (R)—CHBN

The optical purity of (R)—CHBN was determined as described below.

To 1 μl of (R)—CHBN, 20 μl of dichloromethane and 20 μl d of pyridine were added. Then, 2 μl of (R)-α-methoxy-α-(trifluoromethyl)phenylacetyl chloride (MTPA) was added thereto, and the resultant mixture was agitated for 5 hr at room temperature. After completion of the reaction, 300 μl of diisopropyl ether was added to the reaction solution, which was then washed with 350 μl of 1N HCl aqueous solution to collect the organic layer. This organic layer was washed with 350 μl of saturated aqueous sodium hydrogencarbonate solution and vacuum dried. The residue was dissolved in isopropanol and subjected to HPLC analysis.

The HPLC system used in this analysis was as described below.

Target Compounds for Analysis (R)—CHBN MTPA ester (S)—CHBN MTPA ester

Column: Partisil-5 (GL Science), 4.6 mm×250 mm

Column Oven Temperature: 40° C.

Mobile Phase: hexane:isopropanol=99:1, 1 mL/min

Detector: UV 254 nm

| Retention Time: | (R)-CHBN MTPA ester | 11.9 min |
| --- | --- | --- |
| | (S)-CHBN MTPA ester | 13.0 min |

Analysis Method (6)

Determination of the Optical Purity of L-Carnitine

The optical purity of L-carnitine was determined as described below according to the disclosure in *J. Pharm. Bio. Anal.*, 14 (1996)1579-1584.

To a dry carnitine sample whose optical purity is to be determined, 2 mg/ml 9-anthroylnitrile in DMSO (1 ml) and 0.1 mg/ml quinuclidine in acetonitrile (1 ml) are added and dissolved. The resultant solution is reacted at 80° C. for 90 min. After cooled to room temperature, the reaction solution was loaded on a silica gel cartridge column (1 cc Bond Elut; Varian) to wash out the unreacted 9-anthroylnitrile and quinuclidine with 10 ml of methanol/acetonitrile=9:1 solution. Subsequently, 5 ml of ultrapure water is fed to the column, and the resultant solution is subjected to the following HPLC analysis.

Target Compounds for Analysis

L-carnitine

D-carnitine

Column: Ultron ES-OVM (Shinwa Chemical Industries), 2.0 mm×150 mm

Column Oven Temperature: 40° C.

Mobile Phase: acetonitrile/20 mM KH$_2$PO$_4$ (pH 4.5)=17/83

Flow Rate: 0.2 ml/min

Detector: UV 254 nm

Sample volume: 25 μl

Retention Time: L-carnitine 6.8 min

D-carnitine 5.2 min

The optical purity of L-carnitine is calculated by formula below from the respective areas of D-carnitine and L-carnitine.

Optical purity (% ee)=(L-carnitine area−D-carnitine area)/(L-carnitine area+D-carnitine area)×100

I. Synthesis of 4-Chloro-3-Hydroxybutyronitrile (CHBN)

Example 1

Epichlorohydrin+Hydrogen Cyanide→CHBN Synthesis (see Japanese Unexamined Patent Publication No. 2002-241357)

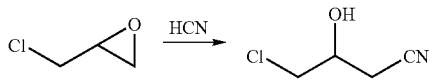

To a 3 L separable flask equipped with an agitator, a thermometer and a Dimroth condenser, 274.93 g (2.97 mol) of epichlorohydrin, 1271.3 g of water and 191.75 g (1.35 mol) of sodium sulfate were placed. While agitating the mixture in warm water bath, 72.3 g (2.70 mol) of hydrogen cyanide was directly supplied to the reaction solution over 1 hr at internal temperatures of 50-60° C. Then, the reaction solution was aged at internal temperatures of 50-60° C. for 6 hr. After cooling the reaction solution in water bath, the solution was extracted once with 1 L of ethyl acetate. Vacuum concentration of the organic layer yielded 249.33 g of crude CHBN. The results of GC analysis revealed that its purity is 80.9% and the yield is 62.5%. The above-mentioned extracted CHBN (crude product) was purified by simple distillation to thereby obtain 187.51 g of purified product.

Example 2

Epichlorohydrin+Sodium Cyanide→CHBN Synthesis (see Japanese Unexamined Patent Publication No. 2004-182607)

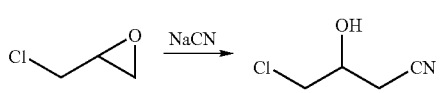

To a tightly sealed glass flask equipped with an agitator, a dropping funnel, a thermometer and a pH meter, 262.3 g of epichlorohydrin and 700 g of water were placed under a nitrogen atmosphere. While controlling the pH of the reaction solution at 8, 432.3 g (2.7 mol) of 30.6 wt % aqueous sodium cyanide solution and 203.7 g (1.35 mol) of 65 wt % aqueous sulfuric acid solution were simultaneously added thereto dropwise over 3 hr at 40° C. under agitation. After the addition, the resultant solution was reacted at 40° C. for 5 hr under agitation. Subsequently, while the glass flask was tightly sealed, 250 ml of ethyl acetate was added, followed by extraction operation at 40° C. The contents of flask were transferred into a separating funnel to thereby obtain the organic layer. Vacuum concentration at 50° C. and vacuum distillation of the resultant organic layer yielded 190.6 g of CHBN. The real yield of the resultant CHBN was 58.1%.

Example 3

1,3-Dichloro-2-Propanol+Sodium Cyanide→CHBN Synthesis

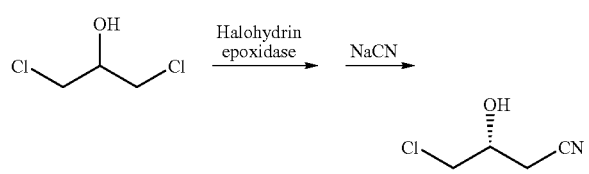

i) Culture of Halohydrin Epoxidase-Expressing Transformant Microorganism

*Escherichia coli* JM109/pST111 (FERM ABP-10922; see Japanese Unexamined Patent Publication H5-317066) with halohydrin epoxidase activity was inoculated into 500 ml Erlenmeyer flasks (n=20) each containing 100 ml of LB medium (1% Bacto tryptone, 0.5% Bacto yeast extract, 0.5% NaCl, 1 mM IPTG, 50 μg/ml ampicillin) and cultured under shaking at 37° C. for 20 hr. The cultured cells in 20 flasks were harvested by centrifugation and washed with 50 mM Tris-sulfate buffer (pH 8.0). To the resultant cells, 50 mM Tris-sulfate buffer (pH 8.0) was added to prepare a 20 g suspension. 0.25 g of this cell suspension was added to 100 ml of 50 mM Tris-sulfate buffer (pH 8.0). To this mixture, 1,3-dichloro-2-propanol was added to give a concentration of 50 mM. The resultant mixture was reacted at 20° C. for 10 min. Quantitative determination of the epichlorohydrin in the reaction solution by HPLC revealed that the concentration was 11 mM.

For information, pST111 is a plasmid obtained by linking to pUC118 a BamHI-PstI fragment (1.1 Kb) comprising a halohydrin epoxidase gene (hheB) derived from *Corynebacterium* sp. N-1074. pST111 is disclosed in Japanese Unexamined Patent Publication No. H5-317066; and JM109/pST111 was deposited under the Budapest Treaty at International Patent Organism Depositary, National Institute of Advanced Industrial Science and Technology (Tsukuba Central 6, 1-1-1 Higashi, Tsukuba City, Ibaraki, Japan) with the accession number of FERM ABP-10922 on Mar. 1, 1991.

ii) Synthesis of (R)—CHBN from 1,3-Dichloro-2-Propanol

To a 500 ml flask equipped with a pH electrode and an alkali feeding pipe controlled by a pH controller, water (170.6 g), 1 mol/kg Tris-sulfate buffer (pH 8.0) (33.5 g) and 6 mol/kg NaCN aqueous solution (57.0 g) were added. The pH of this solution was adjusted to 8.0 with 98% sulfuric acid (15.5 g). 1,3-Dichloro-2-propanol (13.3 g) was added thereto and agitated to give a homogeneous solution.

The pH controller was set to feed 6 mol/kg NaCN aqueous solution so that the pH in the system is maintained at 7.9-8.0. Then, 47.2 g (18.9 kU) of the cell suspension with halohydrin epoxidase activity prepared in i) above was added to the flask, and the reaction was started at 20° C.

While maintaining the pH in the system at 7.9-8.0 at 20° C., from immediately after the start of the reaction, 36.7 g of 1,3-dichloro-2-propanol was added uniformly in a dropwise manner over 4.5 hr. Subsequently, while maintaining the pH in the system at 7.9-8.0 at 20° C., the reaction was continued for another 1.5 hr (total 6 hr from the start of the reaction). At the completion of the reaction, 6 mol/kg NaCN aqueous solution had been added in an amount of 54.4 g, and the amount of total reaction solution was 428.2 g. At that time, the concentration of 1,3-dichloro-2-propanol in the system was 3.7% (15.8 g) and the concentration of 4-chloro-3-hydroxybutyronitrile was 7.1% (30.4 g; yield 65.6%). Further, the optical purity of 4-chloro-3-hydroxybutyronitrile at that time was 92% ee ((R) enantiomeric excess).

This reaction solution was adjusted to pH 5.0 with hydrochloric acid, and HCN was removed at 60° C. under reduced pressure (140 Torr) for 11 hr. Then, the HCN within the system was titrated with silver nitrate to thereby confirm that HCN concentration was 1 ppm or less.

Example 4

1,3-Dichloro-2-Propanol+Hydrogen Cyanide→CHBN Synthesis

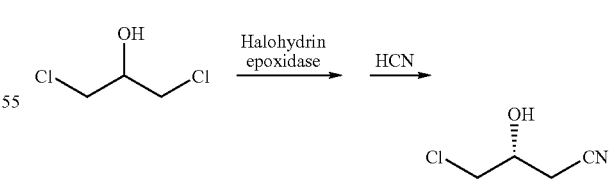

i) Culture of a halohydrin epoxidase-expressing transformant microorganism was performed in the same manner as described in Example 3.

ii) Synthesis of (R)—CHBN from 1,3-Dichloro-2-Propanol

To a 300 ml four-necked flask equipped with a pH electrode and an alkali feeding pipe controlled by a pH controller, 127.55 g of water and 4.41 g of HCN (0.1632 mol) were added. The pH of this solution was adjusted to 7.5 with 0.65 g of 30% NaOH (0.0049 mol). 10.00 g of 1,3-dichloro-2-propanol (0.0775 mol) was added thereto and agitated to give a homogeneous solution.

Then, 20.00 g of the cell suspension with halohydrin epoxidase activity prepared in i) above was added to the flask, and the reaction was started at 20° C. The pH controller was set to feed 30% NaOH so that the pH in the system is maintained at 7.5-7.6. By supplying 1,3-dichloro-2-propanol and HCN at almost equimolar ratios relative to the NaOH fed, the concentrations of 1,3-dichloro-2-propanol and HCN in the system were controlled below 0.5 mol/kg and 1.1 mol/kg, respectively After 23 hr, 4-chloro-3-hyroxybutyronitrile was accumulated at 0.753 mol/kg. The optical purity thereof was 94.8% ee ((R) enantiomeric excess). The yield from the 1,3-dichloro-2-propanol consumed in the reaction was 96.3%.

This reaction solution was adjusted to pH 5.0 with hydrochloric acid, and HCN was removed at 60° C. under reduced pressure (140 Torr) for 11 hr. Then, the HCN within the system was titrated with silver nitrate to thereby confirm that HCN concentration was 1 ppm or less.

II. Synthesis of 4-halogeno-3-hydroxybutyramide

Example 5

The nitrilehydratase used in the present invention was prepared as described below.
(Culture and Method of Preparation of Cell Suspension for Reaction)
*Rhodococcus rhodochrous* J-1 (FERM BP-1478) with nitrilehydratase activity was inoculated into a 30 L jar fermentor (Takasugi-ss Co.) containing 20 L of a medium (pH 7.0) containing glucose 2 mass percent; urea 1 mass percent; peptone 0.5 mass percent; yeast extract 0.3 mass percent; and cobalt chloride 0.05 mass percent, and cultured aerobically at 30° C. for 60 hr. The thus obtained cells were harvested by centrifugation, washed with an equal volume of 50 mM phosphate buffer (pH 7.7) twice and suspended to thereby prepare a cell suspension for reaction.

Example 6

CHBA Synthesis from CHBN (Example 1)

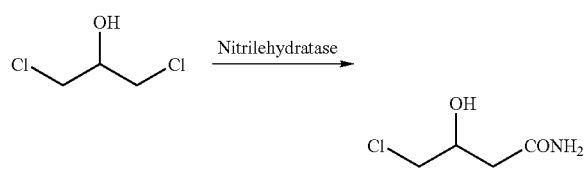

A part of the purified product CHBN synthesized in Example 1 was taken (16 g; 134 mmol) and heated at 130° C. for 2 hr. After cooling, 84 g of 20 mM phosphate buffer (pH 7.5) was added. Then, 200 µl of J-1 cells prepared in Example 5 was added dropwise, and the reaction was started at 2° C. in ice bath. After 3 hr, the conversion rate of CHBN reached 100% and it was confirmed that 18.3 g of CHBA was produced (yield: 99.3%).

A part of the above reaction completed solution (50.1 g; containing 9.20 g of CHBA) was taken, and 5 g of Celite was added thereto. This mixture was exsiccated in an evaporator at 40° C. The residue was placed on silica gel (30 g) and eluted with ethyl acetate (400 g) as a carrier. Exsiccation of the thus eluted ethyl acetate solution in an evaporator yielded 7.27 g of CHBA white solid (isolation yield: 79%).

Example 7

CHBA Synthesis from CHBN (Example 2)

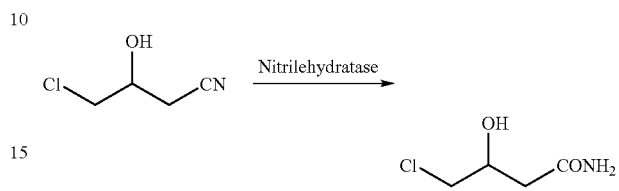

A part of the distilled product CHBN synthesized in Example 2 was taken (1.6 g; 13.4 mmol). 8.4 g of 20 mM phosphate buffer (pH 7.5) was added thereto. Then, 388 µl of 1 mg/ml $CoCl_2.6H_2O$ aqueous solution was added and agitated for 2 hr. Subsequently, 20 µl of J-1 cells prepared in Example 5 was added dropwise, and the reaction was started in ice bath. After 3 hr, the conversion rate of CHBN reached 100% and it was confirmed that 1.84 g of CHBA was produced (yield: 99.88%).

Example 8

CHBA Synthesis from CHBN (Example 3)

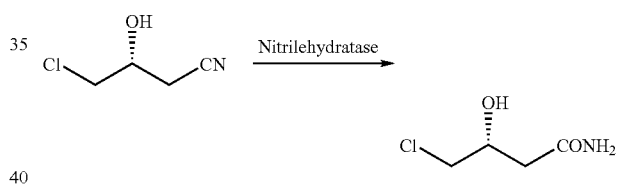

A part of the (R)—CHBN aqueous solution synthesized in Example 3 was taken (10.0 g) ((R,S)—CHBN concentration 16.7%; containing 13.97 mmol) and heated at 100° C. for 4 hr. After cooling, the solution was neutralized with aqueous NaOH to make its pH 7.02. Then, 63 µl of J-1 cells prepared in Example 5 was added dropwise, and the reaction was started in ice bath. After 2 hr, the conversion rate of CHBN reached 100% and it was confirmed that 1.91 g of (R)—CHBA was produced (yield: 99.4%).

Example 9

CHBA Synthesis from CHBN (Example 4)

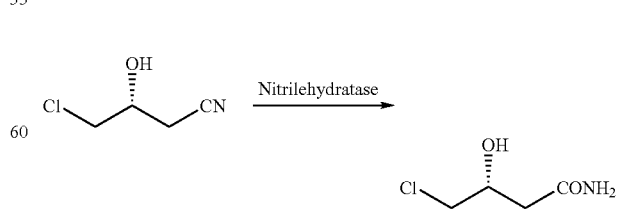

A part of the R)—CHBN aqueous solution synthesized in Example 4 was taken (50.0 g) ((R,S)—CHBN concentration 14.0%; containing 58.6 mmol), and 1.7 ml of 1 mg/ml $CoCl_2$-

6H$_2$O aqueous solution was added thereto. The resultant solution was neutralized with aqueous NaOH to make its pH 7.06 and agitated for 2 hr. Subsequently, 270 µl of J-1 cells prepared in Example 5 was added dropwise, and the reaction was started in ice bath. After 2 hr, the conversion rate of CHBN reached 100% and it was confirmed that 8.04 g of (R)—CHBA was produced (yield: 99.7%).

III. Quaternary Amination Reaction of CHBA (Synthesis of Carnitinamide Chloride)

Example 10

Quaternary Amination Reaction of Purified CHBA

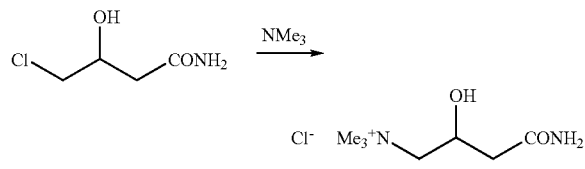

To the purified CHBA synthesized in Example 6 (1.84 g; 13.4 mmol), purified water was added to give a 10.2 g solution. To this solution, 30% aqueous trimethylamine solution (3.15 g; 16.0 mmol) was added and the reaction was started at 30° C. After 4 hr, the conversion rate of CHBA reached 100% and it was confirmed that 2.48 g of Car-amide (yield 94.0%) and 0.071 g of HCAm (yield 5.2%) were produced.

COMPARATIVE EXAMPLE 1

Quaternary Amination Reaction of Purified CHBN (from Example 1)

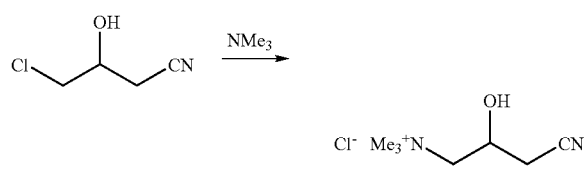

To the purified CHBN synthesized in Example 1 (1.6 g; 13.4 mmol), purified water was added to give a 10.2 g solution. To this solution, 30% aqueous trimethylamine solution (6.60 g; 33.5 mmol) was added and the reaction was started at 30° C. After 7 hr, the conversion rate of CHBN reached 100% and it was confirmed that 1.56 g of Car-nitrile was produced (yield 65.1%).

COMPARATIVE EXAMPLE 2

Quaternary Amination Reaction of Methyl 4-Chloro-3-Hydroxybutyric Acid

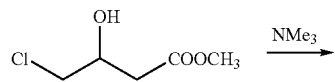

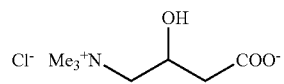

To methyl 4-chloro-3-hydroxybutyric acid (2.0 g; 13.1 mmol), purified water was added to give a 10.0 g solution. To this solution, 30% aqueous trimethylamine solution (5.16 g; 26.2 mmol) was added and the reaction was started at 30° C. In the course of the reaction, γ-hydroxybutyrolactone was observed. Seven hours after the start of the reaction, the conversion rate of methyl 4-chloro-3-hydroxybutyric acid reached 100%. At that time, it was confirmed that the methyl group of the ester and γ-hydroxybutyrolactone were eliminated and that 0.36 g of Car was produced (yield 17.1%). The results of 1H, 13C-NMR measurement confirmed that 3,4-dihydroxybutyric acid was also produced in addition to Car.

Example 11

Quaternary Amination Reaction of CHBA (Aqueous Solution from Example 7)

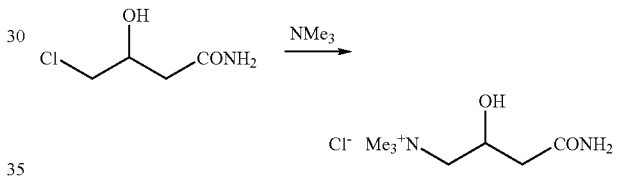

To the reaction completed solution of Example 7 (10.18 g; containing 1.84 g of CHBA), 30% aqueous trimethylamine solution (21.15 g; 107.3 mmol) was added and the reaction was started at 30° C. After 0.75 hr, the conversion rate of CHBA reached 100%, and it was confirmed that 2.55 g of Car-amide (yield 96.9%) and 0.057 g of HCAm (yield 4.2%) were produced.

Example 12

Quaternary Amination Reaction of CHBA (Aqueous Solution from Example 9)

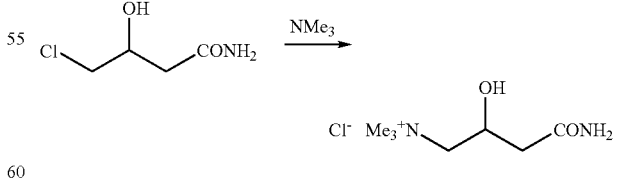

Immediately after the completion of the reaction in Example 9, 26.0 g of the reaction solution (containing 4.02 g of CHBA) was taken. Then, 30% aqueous trimethylamine solution (8.3 g; 35.0 mmol) was immediately added thereto and the reaction was started in 30° C. water bath. After 4 hr, the conversion rate of CHBA reached 100%, and it was confirmed that 5.42 g of Car-amide (yield 94.4%) and 0.15 g of HCAm (yield 5.0%) were produced.

Example 13

Quaternary Amination Reaction of CHBA (Aqueous Solution from Example 9)

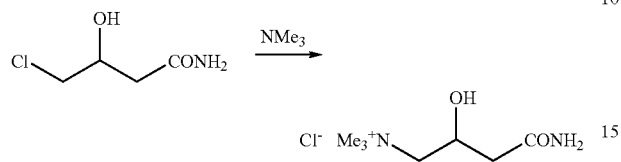

Immediately after the completion of the reaction in Example 9, 26.0 g of the reaction solution (containing 4.02 g of CHBA) was taken and left at 20° C. for 15 hr. The results of HPLC analysis revealed that CHBA decreased to 2.84 g. To the resultant solution, 30% aqueous trimethylamine solution (8.3 g; 35.0 mmol) was added, and the reaction was started in 30° C. water bath. After 4 hr, the conversion rate of CHBA reached 100%, and it was confirmed that 3.84 g of Car-amide (yield 94.6%) and 0.10 g of HCAm (yield 4.8%) were produced. Based on the amount of CHBA immediately after the completion of amidation reaction in Example 9 (4.02 g), the yield of Car-amide is 66.8% and that of HCAm is 3.4%.

The quaternary amination reactions described so far may be summarized as follows. The advantage of using CHBA as a substrate for quaternary amination reaction is evident.

started at 50° C. After 5 hr, the conversion rate of Car-amide reached 100% and the reaction was completed. After neutralization of the system with aqueous HCl, water was removed in an evaporator under reduced pressure. Subsequently, 10 ml of ethanol was added thereto, followed by azeotropic distillation to remove the remaining water. This azeotropic distillation with ethanol was performed 3 times in the total. To the resultant white solid, 10 ml of ethanol was added again and agitated. Undissolved white solid (which is NaCl) was filtered by vacuum filtration. Quantitative determination of Car in the filtrate revealed that 1.94 g of Car (yield 96.6%) and 0.03 g of CB (1.5 wt % relative to Car) were produced.

Example 15

Synthesis of Car from Car-Amide (Example 12)

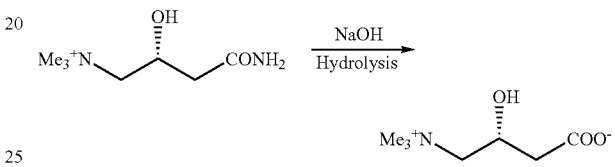

To the reaction completed solution in Example 12 (16.37 g; containing 2.59 g of Car-amide), 48% aqueous NaOH (2.2 g; 26.4 mmol) was added and the reaction was started at 30° C. After 8 hr, when the conversion rate of Car-amide reached 80%, the reaction temperature raised to 40° C., at which the reaction was continued for another 6 hr. Then, the conversion

| | Substrate | Equivalent Number of NMe3 | Reaction Temperature (° C.) | Reaction Time (h) | Yield of Quaternary Aminated Product (%) |
|---|---|---|---|---|---|
| Example 10 | CHBA | 1.19 | 30 | 4 | 94.0 |
| Example 11 | CHBA | 7.98 | 30 | 0.75 | 96.9 |
| Example 12 | (R)CHBA | 1.21 | 30 | 4 | 94.4 |
| Example 13 | (R)CHBA | 1.70 | 30 | 4 | 94.6 |
| Comparative Example 1 | CHBN | 2.50 | 30 | 7 | 65.1 |
| Comparative Example 2 | Methyl 4-chloro-3-hydroxybutyric acid | 2 | 30 | 7 | 17.1 (Car) |

IV. Hydrolysis Reaction of Carnitinamide Chloride

Example 14

Hydrolysis Reaction of Car-Amide (Aqueous Solution from Example 10)

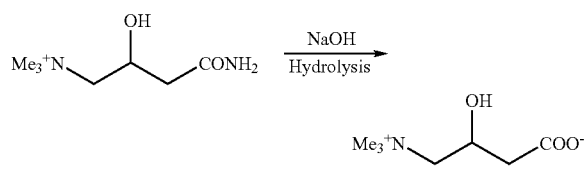

To the reaction completed solution in Example 10 (13.20 g; containing 2.45 g of Car-amide), 30% aqueous NaOH solution (2.68 g; 20.0 mmol) was added and the reaction was rate of Car-amide reached 100% and the reaction was completed. After neutralization of the system with aqueous HCl, (L)-Car and CB in the reaction solution were quantitatively determined. As a result, it was found that 2.09 g of (L)-Car (yield 98.5%) and 0.015 g of CB (0.7% relative to Car) were produced. A part of this aqueous solution was taken, dried and subjected to measurement of the optical purity of Car. As a result, the optical purity was found to be 94.2% ee.

Example 16

Synthesis of Car from Car-Amide (Example 12)

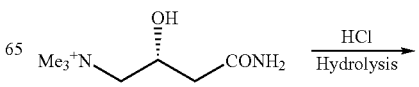

-continued

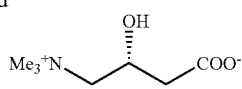

To the reaction completed solution in Example 12 (16.37 g; containing 2.59 g of Car-amide), 36% aqueous HCl (4.01 g; 39.6 mmol) was added and the reaction was started at 80° C. After 8 hr, the conversion rate of Car-amide reached 100% and the reaction was completed. After neutralization of the system with aqueous NaOH (L)-Car and CB in the reaction solution were quantitatively determined. As a result, it was found that 2.11 g of (L)-Car (yield 99.4%) and 0.001 g of CB (yield 0.05%) were produced. A part of this aqueous solution was taken, dried and subjected to measurement of the optical purity of Car. As a result, the optical purity was found to be 94.5% ee.

INDUSTRIAL APPLICABILITY

According to the present invention, a process for preparing a betaine is provided. The present invention is advantageous because the process of the present invention prevents side reactions greatly compared to conventional processes and is capable of producing a betaine, such as carnitine, at a high yield.

The invention claimed is:

1. A process for preparing a 4-trialkylamino-3-hydroxybutyramide halide represented by formula (2') below:

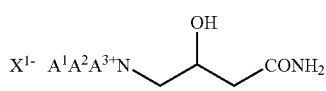

(2')

wherein $A^1$, $A^2$ and $A^3$ are independent from each other, may be the same or different, and individually represent a $C_1$-$C_{20}$ hydrocarbon group which may have a substituent(s), and $X^1$ is a halogen atom; said process comprising a step of quaternary aminating 4-halogeno-3-hydroxybutyramide represented by formula (2) below:

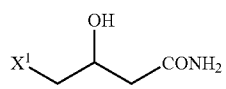

(2)

wherein $X^1$ is a halogen atom; with a trialkylamine represented by $(NA^1A^2A^3)$.

2. The process according to claim wherein said trialkylamine is trimethylamine.

3. A process for preparing a betaine represented by formula (1) below or a salt thereof:

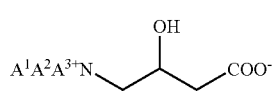

(1)

wherein $A^1$, $A^2$ and $A^3$ are independent from each other, may be the same or different, and individually represent a $C_1$-$C_{20}$ hydrocarbon group which may have a substituent(s);

said process comprising a step of hydrolyzing a halogenated 4-trialkylamino-3-hydroxybutanamide represented by formula (2') below obtained by the method according to claim 1:

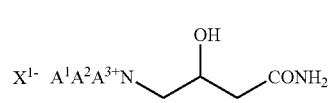

(2')

wherein $A^1$, $A^2$ and $A^3$ are independent from each other, may be the same or different, and individually represent a $C_1$-$C_{20}$ hydrocarbon group which may have a substituent(s), and $X^1$ is a halogen atom.

4. The process according to claim 3, wherein $A^1$, $A^2$ and $A^3$ individually represent a methyl group.

5. The process according to claim 1, wherein said 4-halogen-3-hydroxybutyramide represented by formula (2) below:

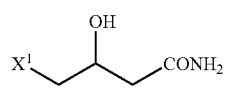

(2)

wherein $X^1$ is a halogen atom;

is obtained by a step of amidating 4-halo-3-hydroxybutyronitrile represented by formula (3) below:

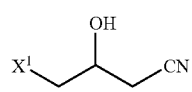

(3)

wherein $X^1$ is a halogen atom.

6. The process according to claim 5, wherein the amidation is performed with a nitrilehydratase.

7. The process according to claim 6, wherein the nitrilehydratase is produced by a microorganism selected from the group consisting of microorganisms belonging to the genuses *Achromobacter, Acidovorax, Agrobacterium, Arthrobacter, Bacillus, Brevibacterium, Burkholderia, Candida, Caseobacter, Comamonas, Corynebacterium, Dietzia, Enterobacter, Erwinia, Geobacillus, Gordona, Klebsiela, Microascus, Morganella, Pantoea, Proteus, Pseudomonas, Pseudonocardia, Rhodococcus, Rhizobium, Serratia, Streptomyces, Syctalidium* and *Tukamurella*.

8. The process according to claim 5, wherein the step of preparing said 4-halogeno-3-hydroxybutyramide is performed at temperatures within a range from a temperature at which the reaction solution does not freeze to about 5° C.

9. The process according to claim 5, wherein said 4-halo-3-hydroxybutyronitrile represented by formula (3) below:

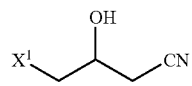

(3)

wherein $X^1$ is a halogen atom;

is obtained by a step of reacting an epihalohydrin represented by formula (4) below:

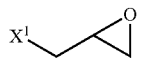
(4)

wherein X¹ is a halogen atom;
or 1,3-dihalo-2-propanol represented by formula (5) below:

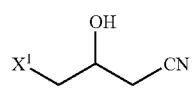
(5)

wherein X¹ is as defined above;
and X² is independent from X¹ and represents an identical or different halogen atom;
with hydrogen cyanide or a cyanide salt.

10. The process according to claim 9, wherein the reaction with hydrogen cyanide or a cyanide salt is performed in the presence of an enzyme catalyst.

11. The process according to claim 10, Wherein said enzyme catalyst is a halohydrin epoxidase.

12. The process according to claim 11, wherein said 4-halo-3-hydroxybutyronitrile represented by formula (3) below:

(3)

wherein X¹ is a halogen atom;
is produced in an (R)-isomer excessive manner.

13. The process according to claim 11, wherein said halohydrin epoxidase is produced by a microorganism selected from the group consisting of microorganisms belonging to the genuses *Corynebacterium, Microbacterium, Agrobacterium, Mycobacterium* and *Arthrobacter*.

* * * * *